United States Patent [19]

Ghosh-Dastidar

[11] Patent Number: 4,770,993
[45] Date of Patent: Sep. 13, 1988

[54] HYBRIDOMA TUMOR CELL LINES AND THEIR MONOCLONAL ANTIBODIES TO THAUMATIN

[75] Inventor: Pradip Ghosh-Dastidar, Los Angeles, Calif.

[73] Assignee: Beatrice Companies, Inc., Chicago, Ill.

[21] Appl. No.: 794,247

[22] Filed: Oct. 31, 1985

[51] Int. Cl.$^4$ .......................................... G01N 33/577
[52] U.S. Cl. .......................................... 435/7; 435/68;
435/172.2; 435/240.27; 435/948; 436/501;
436/518; 436/540; 436/541; 436/543; 436/548;
436/815; 530/387; 530/413; 530/808; 530/809
[58] Field of Search .................. 435/7, 68, 172.2, 240,
435/241, 948; 436/501, 518, 540, 541, 543, 815,
548, 86; 530/300, 387, 388, 801, 809

[56] References Cited

U.S. PATENT DOCUMENTS 4,376,110  3/1983  David et al. ...................... 436/513

OTHER PUBLICATIONS

Haugh et al., Nature, vol. 271, pp. 381–383, 1978.
Edwardson et al., Chemical Abstracts, vol. 88, No. 19, Abstract #132122t, 1978.
Kohler et al., Nature, vol. 256, pp. 495–497, 1975.
Iyengar et al., "The Complete Amino Acid Sequence of the Sweet Protein Thaumatin I", Eur. J. Biochem. 96, pp. 193–204, (1979).
Science News, vol. 127, p. 186, Mar. 23, 1985.

Primary Examiner—Christine M. Nucker
Attorney, Agent, or Firm—Marshall, O'Toole, Gerstein, Murray & Bicknell

[57] ABSTRACT

Disclosed are murine-derived hybridoma tumor cell lines and monoclonal anti-thaumatin antibody substances produced by these cell lines. The monoclonal antibody substances may be used alone or in combination in immunological procedures for isolation of thaumatin and for quantitative detection of thaumatin in fluid samples.

20 Claims, No Drawings

HYBRIDOMA TUMOR CELL LINES AND THEIR MONOCLONAL ANTIBODIES TO THAUMATIN

BACKGROUND OF THE INVENTION

The present invention relates generally to materials and methods for use in immunological procedures for isolation and quantitative detection of a sweet tasting polypeptide known as thaumatin, from biological fluids. More specifically, the invention relates to monoclonal antithaumatin antibodies, produced by novel hybridoma cell lines (as exemplified by A.T.C.C. HB-8921 and A.T.C.C. HB-8922) and to uses of these antibodies in isolation of thaumatin through affinity purification techniques, in assays for detection of thaumatin, and in immunological techniques for study of sweet thaumatin-like polypeptides.

Thaumatin is an extremely sweet-tasting protein produced in the arils of the fruit of the African shrub *Thaumatococcus daniellii* Benth. The fruit traditionally has been used in West Africa as a sweetener of palm wine, corn, bread and sour fruit. Thaumatin, which is about 5000 times sweeter than sucrose on a weight basis, is produced in at least five forms: thaumatins I, II, a, b and c. These proteins, named in their order of elution from an ion exchange column [Higgenbotham, et al., in *Sensory Properties of Foods* (Birch, et al., eds.), London: Applied Sciences, pp. 129–149 (1977)], have molecular weights of approximately 22 kilodaltons.

Thaumatin I and II are non-toxic proteins, are low calorie and non-cariogenic, and elicit profound taste responses suggesting a stable interaction between these proteins and human taste buds. Therefore, thaumatin has potential for use as a sugar substitute, food additive, a sweetness receptor probe and a tool for further elucidation of the taste response.

A plentiful supply of pure thaumatin is required to utilize the protein as a possible food additive and research tool. Because *T. daniellii* requires a tropical climate and insect pollination for successful fruit propagation, there are considerable difficulties involved in greenhouse cultivation of the fruit. For these reasons, considerable effort has been directed toward the introduction of genes into recombinant microorganisms enabling them to synthesize thaumatin. One research group reported an amino acid sequence for thaumatin I. Iyengar, et al., *Eur.J.Biochem.*, 96, 193–204 (1979)]. The research group also reported the successful cloning of a gene for thaumatin II from messenger RNA-dervived cDNA [Edens, et al., *Gene*, 18, 1–12 (1982)]. The Edens, et al. reference cited above notes that a polypeptide having the native sequence of preprothaumatin II has been microbially produced. More specifically, the reference and European Patent Application Nos. 54,330 and 54,331 disclose cDNA sequences coding for native mature thaumtin II and preprothaumatin II and also disclose cloning vehicles comprising the DNA sequences for use in transformation in microorganisms.

In co-owned and copending U.S. patent application No. 540,634 filed Oct. 11, 1983, the successful synthesis of "manufactured" genes coding for thaumatin I having a primary structural conformation duplicating the sequence provided in Iyengar, et al. was disclosed along with their expression in bacterial and yeast hosts.

Of interest to the background of the invention is current research focused on hybridoma techniques for producing tumor cell lines which will manufacture highly specific monoclonal antibodies to a selected antigenic substance. Techniques for the production of monoclonal antibodies are generally well known in the art. Typical descriptions of these procedures may be found in Wands, J. R., and Zurawski, V. R., Gastroenterology 80:225 (1981); Marshak-Rothstein, etal., J. Immunol. 122:2491 (1979); and Oi, V. T. and L. A. Herzenberg, "Immunoglobulin Producing Hybrid," Mishell, B. B. and S. M. Shiigi (eds.) *Selected Methods in Cellular Immunology*, San Francisco: W. H. Freeman Publishing, 1979. Briefly summarized, lymphocytes removed from the spleen of an animal previously injected with the antigen of interest are induced to fuse with myeloma cells in the presence of polyethylene glycol. Thousands of "hybrid" myeloma cells are produced from the fusion. The supernatant from growth of each "hybridoma" cell culture is tested for the presence of the desired antibody activity. When such activity is found in the supernatant of one cell culture, it is cloned by limiting dilutions, and the clones are individually assayed for supernatant activity.

Due to the highly specific nature of their immunological properties, monoclonal antibodies developed according to hybridoma techniques have been proposed for use as diagnostic reagents, therapeutic agents, and agents for affinity purification of specifically cross-reactive antigenic proteins from crude sources. See, e.g., *Trends in Biotechnology*, Vol. 3, No. 7 (July, 1985) and U.S. Pat. Nos. 4,465,624, 4,514,505 and 4,514,507.

While there exists a substantial need for specific monoclonal antibodies for use in detecting, isolating, purifying and studying thaumatin and thaumatin-like polypeptide molecules, there have been no reports of the successful use of hybridoma techniques in obtaining monoclonal antibodies to thaumatin.

BRIEF SUMMARY

The present invention provides, for the first time hybridoma cell lines which produce monoclonal antibodies specifically immununoreactive with thaumatin. Illustratively the present invention provides a new mouse-mouse hybridoma cell line, A.T.C.C. HB-8922, which produces as a component of the supernatant of its growth in culture a monoclonal antibody specifically reactive with the tertiary globular structure of thaumatin and thaumatin-like polypeptides. The invention also provides a new mouse-mouse hybridoma cell line, A.T.C.C. HB-8921, which produces as a component of the supernatant of its growth in culture a monoclonal antibody specifically immunoreactive with one or more specific amino acid sequences making up the primary polypeptide structure of thaumatin and certain thaumatin-like polypeptides. Tumor cell lines, A.T.C.C HB-8922, and A.T.C.C. HB-8921, are on deposit at the American type culture collection, 12301 Parklawn Dr., Rockville, Md. 20852, a recognized public depository for cell cultures and microorganisms.

As another aspect of the present invention, there is provided a monoclonal antibody specifically immunoreactive with the tertiary globular structure of thaumatin as well as with thaumatin-like polypeptides such as the protein monellin. In addition there is provided a monoclonal antibody specifically immunoreactive with one or more specific amino acid sequences making up the primary structure of thaumatin and thaumatin-like polypeptides.

According to the practice of the present invention, a tumor cell line is produced using a standard immunological technique as described in Oi and Herzenberg, "Immunoglobulin Producing Hybrid", supra. Spleen cells from mice, hyperimmunized with isolated plant thaumatin are fused with a mouse myeloma cell line in the presence of polyethylene glycol. The supernatant from growth of each "hybridoma" cell culture is tested for the presence of the desired antibody activity. A selected hybridoma cell cloned to propagate a cell line can produce an antibody in its growth supernatant which has highly specific antithaumatin activity.

Monoclonal antibodies of the invention and, more specifically, each of the two new monoclonal antibodies produced by hybridomas A.T.C.C. HB-8921, and A.T.C.C. HB-8922 may be employed in immunological procedures for affinity purification and isolation of thaumatin or thaumatin-like polypeptides from a fermentation or other medium. In such a procedure, a selected antibody would be immobilized (e.g., on a column) and the fermentation medium would be contacted with the immobilized antibody. Thaumatin would bind to the antibody and would thereafter be eluted from the immobilized antibody in a highly purified form. Antibodies of the invention may also be employed in immunological procedures for the quantitative detection of thaumatin and thaumatin-like polypeptides, such as monellin, in fermentation or other media. Procedures combining the use of the two different types of monoclonal antibodies could be used to detect the presence and number of thaumatin and thaumatin-like molecules in both their native conformations and denatured states when isolated from fermentation or other medias. The present invention further provides an immunological assay for quantitative detection of thaumatin and thaumatin-like polypeptides through the use of enzyme linked immunosorbent assay techniques (ELISA). Other aspects of the present invention will become apparent upon consideration of the following detailed description.

DETAILED DESCRIPTION

The following examples illustrate practice of the invention in the production of a number of hybridoma cell lines including A.T.C.C. HB-8921, and A.T.C.C. HB-8922, the isolation of antibodies to thaumatin and thaumatin-like polypeptides, and the characterization, amplification and properties of the monoclonal antibodies which each possesses immunological attractions for an antigenic determinant of thaumatin.

More particularly, Examples 1 through 3 are directed to stimulation of a mouse toward production of polyclonal mouse serum antibodies to thaumatin, fusion of mouse spleen cells with mouse myeloma cells, and the screening, cloning and growth of hybridoma cells and isolation of monoclonal antibody therefrom. Examples 4 through 46 relate to the characterization of the monoclonal antibodies so produced through ELISA assays and competitive inhibition assays. Example 47 relates to the amplification of monoclonal antibody yields by the ascites method. Example 48 relates to the isolation and purification of thaumatin and thaumatin-like polypeptides through the use of the monoclonal antibodies of the invention. Example 49 relates to the quantitative detection of thaumatin and thaumatin-like polypeptides through the use of assay techniques utilizing more than one antibody.

EXAMPLE 1

Production of Polyclonal Serum

In the procedure for the production of hybridoma cell lines including A.T.C.C. HB-8921, and A.T.C.C. HB-8922, a BALB/C mouse was twice given intramuscular injections over the period of two months with Freunds complete adjuvent and 25 µg of plant thaumatin I (obtained from Sigma Chemical Co., St. Louis, Mo.) and purified on an ion exchange column according to van der Wel and Loeve, European J. Biochem. 31, 221–225 (1972). At the third month following the first injection, the mouse was reinjected with 20 micrograms of thaumatin I. The mouse was bled from its tail to collect sera prior to immunization, before the third injection of thaumatin and once again four days after the third injection.

Both samples of sera were assayed for anti-thaumatin antibodies using an enzyme linked immunosorbance assay (ELISA) technique. In this technique, natural plant thaumatin was bound onto ELISA plates such that only anti-thaumatin antibodies would bind to them as compared to a control serum obtained from the mice prior to the first injection with thaumatin. Both sera samples assayed positive for anti-thaumatin antibodies but sera obtained from the later bleeding had a two fold or greater titer of antibody than sera from the previous bleeding.

EXAMPLE 2

Cell Fusion

In the hybridoma procedure, cell membranes of spleen and myeloma cells fuse and initially surround a common cytoplasm with two or more nuclei. Several days after fusion of the cell membranes, the nuclei fuse and become capable of synchronous mitosis. As these fused cells divide, a variable number of chromosomes of both fused partners are lost until the hybrid cell lines stabilize. A hypoxanthine aminopterin-thymidine (HAT) media prevents the SP2-0:SP2-0 hybrids from growing. The spleen:spleen cell hybrids generally die after two weeks in culture. Thus only the SP2-0:spleen hybrid cells will grow in the cultures.

Following verification that the inoculated mice were producing polyclonal antibodies to thaumatin in serum, the mouse was bled to death by heart puncture and its spleen removed asceptically. Myeloma cells [(Sp2-0/Ag 14) (Schulman, et al., Nature, 276,269 (1978)] were grown in RPMI 1640 (Irvine Scientific, GIBCO) containing 10% horse serum with 50 µg/ml of gentamycin, 2 mM glutamine, 25 mM Hepes and $10^{-5}$ M β-mercaptoethanol. The spleen was washed twice with RPMI media containing 50 µg/ml of gentamycin, 2 mM glutamine and 25 mM Hepes and perfused with a 25 gauge needle. Centrifugation was used to harvest cells from the perfused media. The spleen cells ($6 \times 10^6$) were next centrifuged at 1000 rpm for 10 minutes in a 50 ml conical tube together with $2.4 \times 10^6$ myeloma cells. The supernatant was aspirated and the cells were placed in a 37° C. bath for five minutes. The spleen cells were then fused with the myeloma cells through the dropwise addition of 1 ml of 34% polyethylene glycol over the period of one minute. Over the next three minutes, 3 ml of serum free RPMI was added. Serum free RPMI was then added at a rate of 2 ml/minute for 5 minutes. Additional serum free RPMI was then added until a total volume of 40 ml was achieved. The mixture was then spun at 1500 rpm on a IEC-Centra-7 centrifuge for 7 minutes. The centrifuge tube was aspirated and the cells were resuspended in (HAT) media. After fusion, the cells were transferred into RPMI media containing 0.088 mg/ml of aminopterin, 1.94 mg/ml of thymidine, and 6.8 mg/ml of hypoxanthine and two drops were plated onto each well of six 96 well culture plates.

After four days, two drops of the RPMI and HAT media were added to each well. After four more days two more drops of the HAT media were added to each well. Clones started to appear after a period of 10-30 days. Thaumatin positive clones as determined by ELISA were serially transferred into 24 well plates in RPMI media containing β-mercaptoethanol, glutamine, horse serum and gentamycin. Once the clones reached confluency, they were tested by ELISA and the thaumatin positive clones were serially transferred into 48 well, 24 well and 6 well plates. Those thaumatin positive clones which survived the scale up procedure were then recloned into 96 well plates at a dilution such that there was 1 cell per three wells.

The recloned cell cultures were stepped up to be grown in larger wells, although at each subsequent stage 40-50% of the clones were lost. The clones were grown in 24 well plates, then 6 well plates and finally in flasks. At the 24 well plate stage, 60 positive clones survived but by the time the cultures had been transformed to flasks, only eleven positive clones for thaumatin had survived the scale-up. These clones were designated numbers: 3, 10, 24, 27, 29, 30, 36, 37, 37[1], 38 and 41. Samples of clone no. 3 were eventually deposited as A.T.C.C. HB-8922, and samples of clone no. 29 were eventually deposited as A.T.C.C. HB-8921, as being representative of two types of anti-thaumatin monoclonal antibodies. When the cultures were scaled up to the flasks the medium was separated from cells by centrifugation and ammonium sulfate was used to precipitate proteins. The precipitates were dissolved in phosphate buffered saline containing 1 mM PMSF (phenyl methyl sulfonyl flouride) and were aliquoted and frozen at −80° C. after dialysis against the same buffer. The cells were then frozen in liquid nitrogen.

EXAMPLE 3

Screening, Cloning and Characterization of Monoclonal Antibodies

The following procedure is utilized to carry out enzyme linked immunosorbance assays (ELISA) for thaumatin. All reactions are carried out at room temperature and the ELISA plate is covered with Saran brand plastic wrap at all stages and is incubated within a humidified chamber. ELISA plates are coated by placing 10 ng of thaumatin I purified according to the procedure of example 1 in 50 μl of 25 mM NaHCO$_3$ (pH 9.2). This is incubated at room temperature for 2 hours. The plates are washed twice with 400 μl of PBS (50 mM potassium phosphate, 150 mM NaCl, (pH 7.4) and Tween 20 (0.05%)) (a detergent manufactured by Sigma Chemical Co.) and then twice with 400 μl water. The plates are then coated with 200 μl of 1% bovine serum albumin (BSA) in PBS-Tween 20 (0.025% solution) for 2 hours at room temperature. The plates are again washed twice with 400 μl of the PBS-Tween solution and twice with water.

Fifty μl of media from the culture to be tested is then added. Normal, unfused myeloma cell (Sp2-0/Ag-14) media is used as the negative control. Mouse serum at a dilution of 1:500 or greater is used as a positive control. The media is then incubated for at least four hours at room temperature. The plates are then again washed twice with 400 μl of PBS-Tween 20 solution and then twice with water. Fifty μl of a 1:100 dilution of rabbit anti-mouse light K and λ chain immunoglobulin is added and this is incubated for 2 hours at room temperature. The plates are again washed twice with 400 μl of 0.5% PBS-Tween 20 solution and twice with water. Fifty μl of conjugated goat anti-rabbit IgG peroxidase at a 1:1000 dilution is then added and incubated for 1 hour at room temperature. The plates are once more washed twice with 400 μl PBS-Tween 20 solution and twice with water.

Fifty μl of O-phenylenediamine dihydrochloride (OPD) solution containing 0.01% of H$_2$O$_2$ is added to each well (OPD solution comprises 18 mg of OPD per 30 ml of staining buffer which itself comprises 4.86 ml of 0.5 M citric acid and 10.28 ml of 0.5 M Na$_2$HPO$_4$ diluted up to 100 ml with water). The H$_2$O$_2$ should be added to the OPD only seconds before application. This mixture is then incubated for 5-15 minutes at room temperature until the reaction is stopped by addition of 50 μl of 4N H$_2$SO$_4$. The optical density of the wells is then measured at 490 nm by a Bio-Tek ELISA reader.

EXAMPLES 4-5

Characterization of Monoclonal Antibodies

In these examples ELISA competition assays were run on monoclonal antibodies produced by clones No. 3 and No. 29 according to the methodology of Example 3 in order to characterize these antibodies in the presence of plant thaumatin I, plant thaumatin II, refolded recombinant yeast-produced thaumatin analogue and a recombinant yeast-produced thaumatin analogue-glutathione adduct.

TABLE 1

| | | Inhibition of Binding (%) | | | |
|---|---|---|---|---|---|
| Example No. | Antibody Source (Clone No.) | Thaumatin I (2 μg) | Thaumatin II (2 μg) | Yeast Refolded Thaumatin (0.8 μg) | Yeast Thaumatin-Glutathione Adduct (2 μg) |
| 4 | No. 3 | 42 | 46 | 31 | 0 |
| 5 | No. 29 | 44 | 55 | 33 | 44 |

Table 1 shows test results for the inhibition of binding of thaumatin I, thaumatin II a recombinant yeast produced thaumatin analogue and a recombinant yeast produced thaumatin analogue-glutathione adduct formed as an intermediate in the refolding of the recombinant product. Each of these thaumatin types was found to compete effectively in the ELISA competition assay with clone No. 3 antibody. The recombinant yeast produced thaumatin analogue-glutathione adduct, however, did not compete in the assay with clone No. 3 antibody thus indicating that this antibody is either directed toward the tertiary structure of the polypeptide or that it is directed toward the primary structure (a continuous sequence of amino acids in the polypeptide) of the polypeptide but that the specific epitopes with which the antibody is reactive are blocked by the formation of the adduct. Clone No. 29 antibody, on the other hand, recognizes thaumatin I and II in their natural conformations as well as refolded recombinant produced thaumatin. It also recognizes the recombinant yeast produced thaumatin analogue-glutathione adduct. This tends to indicate that the antibody of clone No. 29 is not directed toward the tertiary globular structure of the molecule (which is disrupted in the case of the glutathione adduct) but instead is directed toward the primary structure of the polypeptide i.e., its amino acid sequence.

EXAMPLES 6-14

Characterization of Monoclonal Antobodies

In these examples ELISA competition assays were run on monoclonal antibodies produced by clones Nos. 10, 24, 27, 30, 36, 37, 37[1], 38, and 41. Tests were conducted according to the methodology of Example 3 on native thaumatin I in its natural conformation and performic acid oxidized and denatured thaumatin I. The denatured thaumatin I was prepared by incubation of 1 mg of thaumatin I in 0.5 ml of a chilled (4° C.) performic acid solution prepared by mixture of a 98% formic acid solution with a 30% hydrogen peroxide solution at a ratio of 9:1.

TABLE 2

Inhibition of Binding (%)

| Experiment No. | 6 | 7 | 8 | 9 | 10 | 11 | 12 | 13 | 14 |
|---|---|---|---|---|---|---|---|---|---|
| Antibody Source (Clone No.) | 10 | 24 | 27 | 30 | 36 | 37 | 37[1] | 38 | 41 |
| Thaumatin | | | | | | | | | |
| 1.0 μg | — | 66 | 80 | — | 60 | — | 100 | — | 60 |
| 2.0 μg | 76 | — | — | 75 | — | 71 | — | 70 | — |
| Performic Acid Oxidized Thaumatin | | | | | | | | | |
| 7.0 μg | 0 | 0 | 0 | 72 | 0 | 0 | 4 | 0 | 0 |

Table 2 shows that monoclonal antibodies produced by clones Nos. 10, 24, 27, 36, 37, 37[1], 38 and 41 recognize only thaumatin in its natural conformation and not thaumatin denatured by performic acid. This indicates that these clones recognize only the tertiary structure of thaumatin. Clone No. 30 antibody, on the other hand, recognizes both thaumatin in its native conformation and thaumatin denatured by performic acid. Because clone No. 30 antibody recognizes both native and denatured thaumatin it appears to be directed toward the primary structure of the polypeptide (i.e. some portion of the continuous sequence of amino acids in the polypeptide).

EXAMPLES 15-28

Characterization of Monoclonal Antibodies

In this set of examples, monoclonal antibodies produced by clones Nos. 10, 24, 27, 30, 36, 37, 37[1], 38 and 41 were characterized with respect to the binding affinity of their antibodies to differing concentrations of thaumatin I, the related sweet polypeptide monellin and performic acid oxidized thaumatin I by the ELISA competition assay.

ELISA plates were coated with 10 ng of thaumatin according to the procedure of Example 3. At the same time, media containing monoclonal antibodies from the various clones was treated with ammonium sulfate and diluted 100 times. Fifty μl of the ammonium sulfate fraction was then added to various wells in the presence of differing amounts of thaumatin I, monellin (Sigma Chemical Co., St. Louis, Mo.) and performic acid oxidized thaumatin I.

TABLE 3

| | Example No. | | | | | | | | | |
|---|---|---|---|---|---|---|---|---|---|---|
| | 15 | 16 | 17 | 18 | 19 | 20 | 21 | 22 | 23 | 23 |
| | Antibody Source (Clone No.) | | | | | | | | | |
| | 24 | 24 | 27 | 27 | 36 | 36 | 37[1] | 37[1] | 41 | 41 |
| | Optical Absorbance (490 nm) | | | | | | | | | |
| Control | 1.6 | 1.5 | 1.56 | 1.4 | 1.52 | 1.5 | 1.36 | 1.1 | 1.46 | 1.5 |
| Control | 1.56 | 1.5 | 1.55 | 1.4 | 1.56 | 1.5 | 1.3 | 1.06 | 1.5 | 1.56 |
| Thaumatin | | | | | | | | | | |
| 0.1 μg | 1.5 | 1.3 | 1.48 | 1.3 | 1.5 | 1.4 | 0.9 | 0.84 | 1.4 | 1.49 |
| 0.3 μg | 1.4 | 0.89 | 1.3 | 0.73 | 1.5 | 1.4 | 0.5 | −0.01 | 1.43 | 1.38 |
| 0.5 μg | 1.2 | 0.89 | 1.19 | 0.69 | 1.38 | 1.4 | 0.18 | −0.07 | 1.4 | 1.4 |
| 0.8 μg | 0.15 | 0.57 | 1.0 | 0.32 | 1.4 | 1.2 | −0.01 | −0.3 | 1.4 | 1.4 |
| 1.0 μg | 0.93 | 0.50 | 0.94 | 0.3 | 1.4 | 1.1 | 0.113 | −0.29 | 1.2 | 1.3 |
| Monellin | | | | | | | | | | |
| 10 μg | 1.4 | — | 1.2 | — | 1.4 | — | 0.2 | — | 1.4 | — |
| 30 μg | 0.82 | — | 0.64 | — | 1.24 | — | −0.2 | — | 1.19 | — |
| 50 μg | 0.36 | — | 0.34 | — | 1.0 | — | −0.3 | — | 1.13 | — |
| 80 μg | 0.21 | — | 0.0 | — | 0.58 | — | −0.4 | — | 0.92 | — |
| 100 μg | 0.21 | — | 0.01 | — | 0.7 | — | −0.39 | — | 0.82 | — |
| Performic Acid Treated Thaumatin | | | | | | | | | | |
| 0.7 μg | 1.4 | — | 1.5 | — | 1.45 | — | 0.86 | — | 1.5 | — |
| 1.4 μg | 1.4 | — | 1.4 | — | 1.45 | — | 0.84 | — | 1.5 | — |
| 2.1 μg | 1.4 | — | 1.4 | — | 1.49 | — | 0.90 | — | 1.5 | — |
| 3.5 μg | 1.4 | — | 1.4 | — | 1.45 | — | 0.89 | — | 1.5 | — |
| 7.0 μg | 1.4 | — | 1.4 | — | 1.45 | — | 0.95 | — | 1.5 | — |

The ELISA competition assay results as presented in Table 3 indicate that monoclonal antibodies from clones Nos. 24, 27, 36, 371[1] and 41 recognize thaumatin in its native conformation as well as monellin. They do not, however, recognize the performic acid denatured thaumatin. This is an additional indication that antibodies from these clones are specific to some portion of the tertiary structure of thaumatin. It also tends to indicate that thaumatin and monellin share a common epitope recognized by the monoclonal antibodies that may also account for their sweetness.

TABLE 4

| | Optical Absorbance (490 nm) | | | |
|---|---|---|---|---|
| | Example No. | | | |
| | 25 | 26 | 27 | 28 |
| | Antibody Source (Clone No.) | | | |
| | 10 | 30 | 37 | 38 |
| Control | 1.5 | 1.4 | 1.3 | 1.52 |
| Control | 1.5 | 1.35 | 1.4 | 1.5 |
| Thaumatin | | | | |
| 0.2 μg | 0.6 | 0.7 | 0.5 | 1.2 |
| 0.5 μg | 0.35 | 0.4 | 0.4 | 0.9 |
| 2.0 μg | 0.35 | 0.35 | 0.38 | 0.4 |
| 5.0 μg | 0.35 | 0.36 | 0.33 | 0.4 |
| Monellin | | | | |
| 2.0 μg | 0.7 | 0.38 | 0.58 | 1.4 |
| 5.0 μg | 0.35 | 0.35 | 0.49 | 1.2 |
| 10.0 μg | 0.35 | 0.35 | 0.43 | 0.8 |
| Performic Acid Treated Thaumatin | | | | |
| 1.4 μg | 1.5 | 0.4 | 1.36 | 1.5 |
| 7.0 μg | 1.5 | 0.38 | 1.42 | 1.5 |
| 10.0 μg | 1.5 | 0.38 | 1.50 | 1.5 |

The results as presented in Table 4 indicate that monoclonal antibodies produced by clones Nos. 10, 37 and 38 recognize thaumatin I and monellin but do not recognize performic acid denatured thaumatin. This indicates that these antibodies recognize specific portions of the tertiary structure of both thaumatin and monellin. The antibody produced by clone No. 30 on the other hand is inhibited by monellin, native plant thaumatin and denatured thaumatin. This indicates that like the antibody of clone No. 29, the antibody of the clone No. 30 is specifically reactive with some portion of the primary structure of thaumatin as well as of monellin.

EXAMPLES 29–36

Characterization of Monoclonal Antibodies

In this set of examples, monoclonal antibodies from clones No. 3 (A.T.C.C. HB-8922) and No. 29 (A.T.C.C. HB-8921) were selected as being representative of two major antibody types. ELISA plates were coated according to the procedure of Example 3 with 50 μl of either (1) bovine serum albumin (BSA) (10 mg/ml), (2) performic acid treated thaumatin I (21 μg/ml), (3) thaumatin I (1 μg/ml) or (4) monellin (4 μg/ml). Table 5 shows the results of the ELISA procedure which confirms that the clone No. 3 antibody recognizes only monellin and thaumatin which is presented in its native conformation. On the other hand the clone No. 29 antibody recognizes thaumatin, monellin and denatured thaumatin.

TABLE 5

| | | Optical Absorbance (490 nm) | | | |
|---|---|---|---|---|---|
| Example No. | Clone No. | Thaumatin (1 μg/ml) | Monellin (4 μg/ml) | Performic Acid Oxidized Thaumatin (21 μg/ml) | BSA (10 mg/ml) (control) |
| 29 | 3 | 1.5 | 1.47 | 0.286 | −0.146 |
| 30 | 3 | 1.5 | 1.4 | 0.30 | −0.15 |
| 31 | 3 | 1.64 | 1.4 | 0.05 | −0.24 |
| 32 | 3 | 1.62 | 1.4 | 0.06 | −0.21 |
| 33 | 29 | 0.35 | 0.36 | 0.47 | 0.012 |
| 34 | 29 | 0.35 | 0.28 | 0.55 | 0.070 |
| 35 | 29 | 0.39 | 0.22 | 0.4 | 0.10 |
| 36 | 29 | 0.36 | 0.23 | 0.4 | 0.16 |

EXAMPLES 37–40

Characterization of Monoclonal Antibodies

In this set of examples monoclonal antibodies from clones Nos. 3 and 29 were selected as being representative of two major antibody types. ELISA plates were coated according to the procedure of Example 3 with 50 μl of plant thaumatin I (0.2 μg/ml), with thaumatin-glutathione adduct 5 μg/ml) or with bovine serum albumin (BSA) as a control. The adduct is an intermediate in the folding process of recombinant yeast produced Thaumatin I according to the sequence of Iyengar, et al. and is not sweet.

TABLE 6

| | | Optical Absorbance (490 nm) | | |
|---|---|---|---|---|
| Example No. | Clone No. | Thaumatin | Thaumatin-glutathione Adduct | BSA (control) |
| 37 | 3 | 1.4 | 0.11 | 0.08 |
| 38 | 3 | 1.5 | 0.14 | 0.09 |
| 39 | 29 | 0.53 | 0.55 | 0.10 |
| 40 | 29 | 0.47 | 0.48 | 0.10 |

The results presented in Table 6 demonstrate that antibodies produced by clone No. 3 recognize only native plant thaumatin I and do not recognize the unfolded recombinant adduct. Monoclonal antibodies from clone No. 29, however recognize both the native thaumatin as well as the unfolded adduct.

EXAMPLE 41

Competition Assay for Monoclonal Antibodies

In this example, the inhibition effect of recombinant yeast produced thaumatin analogue-glutathione adduct and of performic acid oxidized plant thaumatin on binding of clone No. 3 monoclonal antibodies to native plant thaumatin I was evaluated. ELISA plates were coated with 10 ng of native plant thaumatin I per well. The antibodies were preincubated with control buffer or with various amounts of test materials for 2 hours and were added to the plates. The plates were then developed according to the ELISA procedure of Example 3. The results shown in Table 7 indicate that addition of 500 ng of native thaumatin effectively inhibits the assay by 50%. Preincubation of the clone No. 3 antibody with the thaumatin analogue-glutathione adduct or performic acid oxidized thaumatin results in little or no inhibition in the assay.

TABLE 7

| | Inhibition of Binding (%) | | | | | |
|---|---|---|---|---|---|---|
| Addition | 0 | 100 ng | 200 ng | 500 ng | 1 μg | 2 μg |
| Thaumatin | 0 | 16 | 30 | 50 | 60 | 80 |
| Thaumatin-glutathione adduct | 0 | 0 | 0 | 0 | 6 | 0 |
| Performic acid oxidized thaumatin | 0 | 0 | 0 | 0 | 0 | 6 |

EXAMPLE 42

Competition Assay for Monoclonal Antibodies

In this example inhibition effect of recombinant yeast produced thaumatin analogue-glutathione adduct and of performic acid oxidized thaumatin on binding of clone No. 29 monoclonal antibodies to native plant thaumatin I was evaluated. ELISA plates were coated with 10 ng of native plant thaumatin I per well. The antibodies were preincubated with control buffer or with various amounts of test materials for 2 hours and were added to the plates. The plates were then developed according to the ELISA procedure of Example 3. The results shown in Table 8 indicate that both the thaumatin-glutathione adduct and performic acid oxidized thaumatin compete effectively with native plant thaumatin for Clone No. 29 antibody in the ELISA competition assay.

TABLE 8

| Addition | Inhibition of Binding (%) | | | | | |
|---|---|---|---|---|---|---|
| | 0 | 100 ng | 200 ng | 500 ng | 1 μg | 2 μg |
| Thaumatin | 0 | 5 | 30 | 51 | 65 | 80 |
| Thaumatin-glutathione adduct | 0 | 4 | 31 | 49 | 69 | 84 |
| Performic acid oxidized thaumatin | 0 | 8 | 29.5 | 49 | 64 | 82 |

EXAMPLES 43–45

Characterization of Monoclonal Antibodies

In this set of examples, monoclonal antibodies produced by clones Nos. 3 and 29 were tested for reactivity to the sweeteners monellin, sucrose and aspartame. Media from cultures of the two clones (100 ml each) was precipitated with a 50% supersaturation of ammonium sulfate. The precipitate was then dissolved in 5 ml of PBS (pH 7.4). Protein concentrations for both were 20 mg/ml. The ammonium sulfate concentrated media at dilutions of 1:20 and 1:60 was then checked for reactivity towards the sweeteners.

ELISA plates were coated with native plant thaumatin I (10 ng in 50 μl of 20 mM $NaHCO_3$). Antibodies from clones Nos. 3 and 29 at the two dilutions were preincubated with 0.5 nM monellin, 500 nM sucrose and 170 nM of aspartame for three minutes at 24° C. The plates were developed according to the ELISA competition procedure of Example 3. The results shown in Table 9 indicate that neither of the monoclonal antibodies react with sucrose or with aspartame. The assay also shows that monellin at the concentration presented does not inhibit binding of the antibody produced by clone No. 3 with thaumatin.

TABLE 9

| Example No. | Clone No. | Dilution | Optical Absorbance (490 nm) | | | |
|---|---|---|---|---|---|---|
| | | | Control | Monellin | Sucrose | Aspartame |
| 43 | 3 | 1:20 | 1.6 | 1.69 | 1.59 | 1.54 |
| 43 | 3 | 1:60 | 1.4 | 1.39 | 1.41 | 1.41 |
| 44 | 29 | 1:20 | 1.15 | 0.059 | 1.40 | 1.33 |
| 44 | 29 | 1:60 | 0.365 | 0.016 | 0.310 | 0.210 |
| 45 | 29 | 1:20 | 1.12 | 0.034 | 1.39 | 1.32 |
| 45 | 29 | 1:60 | 0.305 | 0.07 | 0.239 | 0.340 |

EXAMPLE 46

Competitive Assay

In this example a competition assay was conducted between native plant thaumatin I and monellin as described in example 41. The results shown in Tables 10 and 11 indicate that monellin inhibits binding at roughly a ten fold greater concentration than thaumatin. Therefore the monoclonal antibody of clone No. 29 has a ten fold lower affinity for monellin than it does for thaumatin.

TABLE 10

| Protein | Amount of Protein | Inhibition (%) |
|---|---|---|
| Thaumatin | 10 ng | not detectable |
| Thaumatin | 50 ng | not detectable |
| Thaumatin | 100 ng | 25 |
| Thaumatin | 1 μg | 62.5 |
| Thaumatin | 10 μg | 94 |
| Thaumatin | 100 μg | 95 |

TABLE 11

| Protein | Amount of Protein | Inhibition (%) |
|---|---|---|
| Monellin | 10 ng | not detectable |
| Monellin | 50 ng | not detectable |
| Monellin | 100 ng | not detectable |
| Monellin | 1 μg | 15 |
| Monellin | 10 μg | 60 |
| Monellin | 100 μg | 98 |

EXAMPLE 47

Amplification of Antibody Yields by Ascites Method

To obtain a more concentrated antibody than that produced in tissue culture, the monoclonal antibodies of the present invention were amplified by the ascites method generally described in Kenneth, et al. (eds.), *Monoclonal Antibodies, Hybridomas: A New Dimension in Biological Analysis*, p. 403, New York: Plenum Press (1981). According to this procedure, mice were primed with 0.6 ml of Pristane (2,6,19,14-tetra methylpentadecane, obtained from Aldrich Chemical Co.) injected into their peritoneal cavities by means of 25 or 27 gauge needles. Pristane treatment permits the growth of tumor cells in an ascitic form within the peritoneal cavity. After three weeks, $10^6$ hybridoma cells were injected into the peritoneal cavities of the mice along with 0.5 ml of serum-free Dulbecco's modified eagles medium (DMEM) (Irvine Scientific Co.). Two sets of injections were conducted on two mice for each of clones No. 3 and No. 29.

Seven days after the injection of the hybridoma cells, water and food (oatmeal) was provided to the mice in petri dishes. Twelve to forteen days after the injection of the hybridoma cells, ascites fluid was obtained from the intraperitoneal cavities of the mice by making small cuts into the skin and pipetting out the fluid. The fluid was centrifuged and the cells were suspended in freezing media and then frozen in liquid nitrogen. The ascites fluid was then assayed at dilutions of 1:3, 1:9, 1:27, and 1:81 against native thaumatin, monellin and a control (BSA). This procedure produces a smaller volume of monoclonal antibody which has a higher titer than antibody produced in a tissue culture. Ascites fluid antibodies can be further purified from ascites fluid albumin by precipitation with 40% ammonium sulfate and ion exchange chromatography.

EXAMPLE 48

Isolation and Purification of Thaumatin-like Polypeptides

Through its provision of highly specific and highly reactive anti-thaumatin monoclonal antibodies, the present invention makes possible for the first time the isolation of thaumatin and thaumatin-like polypeptides from fermentation cultures as well as from natural plant sources according to affinity purification procedures well known in the art. Briefly put, preferred isolation procedures would involve immobilizing an antibody of the invention on a solid support (e.g., a chromatographic column), contacting the thaumatin containing fluid with the immobilized antibody and thereafter eluting purified thaumatin from immune complex association with the antibody. By adjusting the particular antibody used, the purification technique could be adjusted to isolate native thaumatin in its correctly folded conformation from incorrectly folded or denatured thaumatin. Thaumatin-like peptides could be isolated and studied as could specific antigenic epitopes of thaumatin-like molecules.

EXAMPLE 49

Quantitative Detection of Thaumatin-like Polypeptides

Through its provision of highly specific anti-thaumatin monoclonal antibodies, the present invention also makes possible novel assays for quantitative detection of thaumatin in a fluid sample which employ more than one anti-body. Such assays would include the steps of:

(1) contacting the fluid with a first, immobilized, antibody which reacts with a first antigenic determinant of thaumatin in the fluid to form an immunological complex of thaumatin and the first antibody;

(2) contacting the complex formed in step (1) with a second antibody which reacts with an antigenic determinent of thaumatin other than the first antigenic determinent, to form an immunological complex of thaumatin and the second antibody; and (3) quantifying the amount of the second antibody bound to the immunological complex formed in step (2).

Such assay procedures would preferably include two of the above described monoclonal antibodies, but may also be developed using one of the monoclonal antibodies and a polyvalent serum derived antibody to thaumatin.

Numerous modifications and variation in practice of the invention are expected to occur to those skilled in the art upon consideration of the foregoing descriptions of preferred embodiments thereof. Consequently, only such limitations should be placed on the invention as appear in the following claims.

What is claimed is:

1. A murine derived hybridoma cell line capable of producing in the medium of its growth a monoclonal antibody capable of specifically binding with thaumatin but not capable of specifically binding with L-aspartyl-L-phenylalanine methyl ester.

2. A murine derived hybridoma cell line capable of producing in the medium of its growth a monoclonal antibody capable of specifically binding with monellin.

3. A hybridoma cell line according to claim 1 capable of producing in the medium of its growth a monoclonal antibody capable of specifically binding with an epitope comprising a portion of the tertiary structure of thaumatin.

4. A hybridoma cell line according to claim 1 capable of producing in the medium of its growth a monoclonal antibody capable of specifically binding with an epitope comprising a portion of the primary structure of thaumatin.

5. A hybridoma cell line according to claim 3 which is ATCC No. HB-8922.

6. A hybridoma cell line according to claim 4 which is ATCC No. HB-8921.

7. A monoclonal antibody produced by a hybridoma cell line according to claim 1.

8. A monoclonal antibody produced by a hybridoma cell line according to claim 2.

9. A monoclonal antibody produced by a hybridoma cell line according to claim 3.

10. A monoclonal antibody produced by a hybridoma cell line according to claim 4.

11. A monoclonal antibody produced by a hybridoma cell line according claim 5.

12. A monoclonal antibody produced by a hybridoma cell line according claim 6.

13. In an immunological procedure for isolation of biologically active thaumatin or polypeptides sharing an antigenic epitope with thaumatin from a biological fluid on the basis of a selective immunological reaction with an antibody specific for thaumatin, the improvement comprising: employing the monoclonal antibody of claim 7 as said specific antibody.

14. In an immunological procedure for isolation of biologically active thaumatin or polypeptides sharing an antigenic epitope with thaumatin from a biological fluid on the basis of a selective immunological reaction with an antibody specific for thaumatin, the improvement comprising: employing the monoclonal antibody of claim 9 as said specific antibody.

15. In an immunological procedure for isolation of biologically active thaumatin or polypeptides sharing an antigenic epitope with thaumatin from a biological fluid on the basis of a selective immunological reaction with an antibody specific for thaumatin, the improvement comprising: employing the monoclonal antibody of claim 10 as said specific antibody.

16. In an immunological procedure for isolation of biologically active thaumatin or polypeptides sharing an antigenic epitope with thaumatin from a biological fluid on the basis of a selective immunological reaction with an antibody specific for thaumatin, the improvement comprising: employing the monoclonal antibody of claim 11 as said specific antibody.

17. In an immunological procedure for isolation of biologically active thaumatin or polypeptides sharing an antigenic epitope with thaumatin from a biological fluid on the basis of a selective immunological reaction with an antibody specific for thaumatin, the improvement comprising: employing the monoclonal antibody of claim 12 as said specific antibody.

18. In an immunological procedure for isolation of biologically active monellin from a biological fluid on the basis of a selective immunological reaction with an antibody specific for monellin, the improvememt comprising: employing the monoclonal antibody of claim 8 as said specific antibody.

19. In an immunological assay for quantitative detection of thaumatin or polypeptides sharing an antigenic epitope with thaumatin in a biological fluid comprising the steps of:

(1) contacting the fluid with a first, immobilized, antibody which reacts with a first antigenic determinant of thaumatin in the fluid to form an immunological complex of thaumatin and the first antibody;

(2) contacting the complex formed in step (1) with a second antibody which reacts with an antigenic determinant of thaumatin other than the first antigenic determinant, to form an immunological complex of thaumatin and the second antibody; and (3) quantifying the amount of the second antibody bound to the immunological complex formed in step (2), the improvement comprising:

employing the monoclonal antibody of claim 7 as one of said antibodies.

20. In an immunological assay for quantitative detection of monellin in a biological fluid comprising the steps of:

(1) contacting the fluid with a first, immobilized, antibody which reacts with a first antigenic determinant of monellin in the fluid to form an immunological complex of monellin and the first antibody;

(2) contacting the complex formed in step (1) with a second antibody which reacts with an antigenic determinant of monellin other than the first antigenic determinant, to form an immunological complex of monellin and the second antibody; and (3) quantifying the amount of the second antibody bound in the immunological complex formed in step (2), the improvement comprising:

employing the monoclonal antibody of claim 8 as one of said antibodies.

* * * * *

UNITED STATES PATENT AND TRADEMARK OFFICE
CERTIFICATE OF CORRECTION

PATENT NO. : 4,770,993
DATED     : September 13, 1988
INVENTOR(S) : Ghosh-Dastidar It is certified that error appears in the above-identified patent and that said Letters Patent is hereby corrected as shown below:

Column 1, line 49, change "RNA-dervived" to --RNA-derived--;

column 1, line 56, change "thaumtin" to --thaumatin--;

column 2, line 5, change "etal." to --et al.--;

column 2, line 39, change "immununoreactive" to --immunoreactive--;

column 4, line 49, change "276,269" to --276, 269--;

column 5, line 44, change "Monoclona" to --Monoclonal--;

column 8, line 60, change "$371^1$" to --$37^1$--;

column 12, line 46, change "forteen" to --fourteen--;

column 13, line 22, change "anti-body" to --antibody--;

column 13, lines 28-29, change "determinent" to --determinant--;

column 13, lines 29-30, change "determinent" to --determinant--;

column 14, line 10, between "according" and "claim", insert --to--;

column 14, line 12, between "according" and "claim", insert --to--;

column 16, line 9, change "bound in" to --bound to--.

Signed and Sealed this

Fourth Day of April, 1989

*Attest:*

DONALD J. QUIGG

*Attesting Officer*    Commissioner of Patents and Trademarks